(12) United States Patent
Boismier et al.

(10) Patent No.: US 8,663,313 B2
(45) Date of Patent: Mar. 4, 2014

(54) LOW STRAIN HIGH STRENGTH STENT

(75) Inventors: Dennis A. Boismier, Shorewood, MN (US); Sumit Agrawal, Plymouth, MN (US); Michael P. Meyer, Richfield, MN (US); Rajesh Radhakrishnan, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/240,892

(22) Filed: Sep. 22, 2011

(65) Prior Publication Data

US 2012/0226346 A1 Sep. 6, 2012

Related U.S. Application Data

(60) Provisional application No. 61/448,843, filed on Mar. 3, 2011.

(51) Int. Cl.
*A61F 2/82* (2013.01)

(52) U.S. Cl.
USPC .......................................... 623/1.15

(58) Field of Classification Search
None
See application file for complete search history.

(56) References Cited

U.S. PATENT DOCUMENTS

| | | | |
|---|---|---|---|
| 2,836,181 A | 5/1958 | Tapp | |
| 3,105,492 A | 10/1963 | Jeckel | |
| 3,272,204 A | 9/1966 | Artandi et al. | |
| 3,490,975 A | 1/1970 | Lightwood et al. | |
| 3,509,883 A | 5/1970 | Dibelius | |
| 3,526,228 A | 9/1970 | Lyng | |
| 3,562,820 A | 2/1971 | Braun | |
| 3,635,215 A | 1/1972 | Shea et al. | |
| 3,657,744 A | 4/1972 | Ersek | |
| 3,771,526 A | 11/1973 | Rudie | |
| 3,868,956 A | 3/1975 | Alfidi et al. | |
| 3,993,078 A | 11/1976 | Bergentz et al. | |
| 4,078,167 A | 3/1978 | Banas et al. | |

(Continued)

FOREIGN PATENT DOCUMENTS

| | | |
|---|---|---|
| CA | 2248718 | 9/1997 |
| DE | 29701758 | 3/1997 |

(Continued)

OTHER PUBLICATIONS

International Search Report and Written Opinion, PCT/US2011/052622, mailed Dec. 6, 2011.

(Continued)

*Primary Examiner* — Thomas J Sweet
*Assistant Examiner* — Rebecca Preston
(74) *Attorney, Agent, or Firm* — Vidas, Arrett & Steinkraus

(57) ABSTRACT

In at least one embodiment, a stent comprises an expandable framework comprising a plurality of serpentine bands and a plurality of connector struts. Each serpentine band comprises a plurality of alternating struts and turns. A plurality of the serpentine bands each have their proximal turns aligned on a common stent circumference and comprise first distal turns and second distal turns. The first distal turns are aligned with one another on a common stent circumference. The second distal turns aligned with one another on another common stent circumference. Each band in the plurality comprises first struts and second struts. Each first strut is attached between a proximal turn and a first distal turn, and each second strut is attached between a proximal turn and a second distal turn. The second struts are wider than said first struts.

18 Claims, 6 Drawing Sheets

(56) References Cited

U.S. PATENT DOCUMENTS

| | | | |
|---|---|---|---|
| 4,127,761 | A | 11/1978 | Pauley et al. |
| 4,130,904 | A | 12/1978 | Whalen |
| 4,140,126 | A | 2/1979 | Choudhury |
| 4,141,364 | A | 2/1979 | Schultze |
| 4,164,045 | A | 8/1979 | Bokros et al. |
| 4,214,587 | A | 7/1980 | Sakura, Jr. |
| 4,300,244 | A | 11/1981 | Bokros |
| 4,313,231 | A | 2/1982 | Koyamada |
| 4,319,363 | A | 3/1982 | Ketharanathan |
| 4,425,908 | A | 1/1984 | Simon |
| 4,441,215 | A | 4/1984 | Kaster |
| 4,470,407 | A | 9/1984 | Hussein |
| 4,501,264 | A | 2/1985 | Rockey |
| 4,503,569 | A | 3/1985 | Dotter |
| 4,512,338 | A | 4/1985 | Balko et al. |
| 4,535,770 | A | 8/1985 | Lemole |
| 4,550,447 | A | 11/1985 | Seiler, Jr. et al. |
| 4,553,545 | A | 11/1985 | Maass et al. |
| 4,560,374 | A | 12/1985 | Hammerslag |
| 4,580,568 | A | 4/1986 | Gianturco |
| 4,597,389 | A | 7/1986 | Ibrahim et al. |
| 4,647,416 | A | 3/1987 | Seiler, Jr. et al. |
| 4,649,922 | A | 3/1987 | Wiktor |
| 4,655,771 | A | 4/1987 | Wallsten |
| 4,655,776 | A | 4/1987 | Lesinski |
| 4,665,918 | A | 5/1987 | Garza et al. |
| 4,681,110 | A | 7/1987 | Wiktor |
| 4,693,721 | A | 9/1987 | Ducheyne |
| 4,733,665 | A | 3/1988 | Palmaz |
| 4,739,762 | A | 4/1988 | Palmaz |
| 4,740,207 | A | 4/1988 | Kreamer |
| 4,760,849 | A | 8/1988 | Kropf |
| 4,762,128 | A | 8/1988 | Rosenbluth |
| 4,768,507 | A | 9/1988 | Fischell et al. |
| 4,769,029 | A | 9/1988 | Patel |
| 4,771,773 | A | 9/1988 | Kropf |
| 4,776,337 | A | 10/1988 | Palmaz |
| 4,786,507 | A | 11/1988 | Schmidt |
| 4,787,899 | A | 11/1988 | Lazarus |
| 4,795,458 | A | 1/1989 | Regan |
| 4,795,465 | A | 1/1989 | Marten |
| 4,800,882 | A | 1/1989 | Gianturco |
| 4,820,298 | A | 4/1989 | Leveen et al. |
| 4,830,003 | A | 5/1989 | Wolff et al. |
| 4,842,575 | A | 6/1989 | Hoffman, Jr. et al. |
| 4,848,343 | A | 7/1989 | Wallsten et al. |
| 4,851,009 | A | 7/1989 | Pinchuk |
| 4,856,516 | A | 8/1989 | Hillstead |
| 4,872,874 | A | 10/1989 | Taheri |
| 4,877,030 | A | 10/1989 | Beck et al. |
| 4,878,906 | A | 11/1989 | Lindemann et al. |
| 4,886,062 | A | 12/1989 | Wiktor |
| 4,913,141 | A | 4/1990 | Hillstead |
| 4,922,905 | A | 5/1990 | Strecker |
| 4,950,227 | A | 8/1990 | Savin et al. |
| 4,950,258 | A | 8/1990 | Kawai et al. |
| 4,994,071 | A | 2/1991 | MacGregor |
| 5,015,253 | A | 5/1991 | MacGregor |
| 5,019,090 | A | 5/1991 | Pinchuk |
| 5,035,706 | A | 7/1991 | Giantureo et al. |
| 5,037,392 | A | 8/1991 | Hillstead |
| 5,059,211 | A | 10/1991 | Stack et al. |
| 5,061,275 | A | 10/1991 | Wallsten et al. |
| 5,064,435 | A | 11/1991 | Porter |
| 5,091,205 | A | 2/1992 | Fan |
| 5,091,211 | A | 2/1992 | Richard |
| 5,092,877 | A | 3/1992 | Pinchuk |
| 5,102,417 | A | 4/1992 | Palmaz |
| 5,104,399 | A | 4/1992 | Lazarus |
| 5,104,404 | A | 4/1992 | Wolff |
| 5,108,415 | A | 4/1992 | Pinchuk et al. |
| 5,108,417 | A | 4/1992 | Sawyer |
| 5,122,154 | A | 6/1992 | Rhodes |
| 5,133,732 | A | 7/1992 | Wiktor |
| 5,135,536 | A | 8/1992 | Hillstead |
| 5,139,480 | A | 8/1992 | Hickle et al. |
| 5,147,385 | A | 9/1992 | Beck et al. |
| 5,147,400 | A | 9/1992 | Kaplan et al. |
| 5,158,548 | A | 10/1992 | Lau et al. |
| 5,163,952 | A | 11/1992 | Froix |
| 5,195,984 | A | 3/1993 | Schatz |
| 5,197,978 | A | 3/1993 | Hess |
| 5,217,483 | A | 6/1993 | Tower |
| 5,226,913 | A | 7/1993 | Pinchuk |
| 5,282,823 | A | 2/1994 | Schwartz et al. |
| 5,282,824 | A | 2/1994 | Gianturco |
| 5,292,331 | A | 3/1994 | Boneau |
| 5,304,200 | A | 4/1994 | Spaulding |
| 5,344,425 | A | 9/1994 | Sawyer |
| 5,354,308 | A | 10/1994 | Simon et al. |
| 5,354,309 | A | 10/1994 | Schnepp-Pesch et al. |
| 5,356,423 | A | 10/1994 | Tihon et al. |
| 5,366,504 | A | 11/1994 | Andersen et al. |
| 5,383,892 | A | 1/1995 | Cardon et al. |
| 5,389,106 | A | 2/1995 | Tower |
| 5,405,377 | A | 4/1995 | Cragg |
| 5,411,552 | A | 5/1995 | Andersen et al. |
| 5,443,498 | A | 8/1995 | Fontaine |
| 5,449,373 | A | 9/1995 | Pinchasik et al. |
| 5,522,881 | A | 6/1996 | Lentz |
| 5,591,197 | A | 1/1997 | Orth et al. |
| 5,609,627 | A | 3/1997 | Goicoechea et al. |
| 5,628,782 | A | 5/1997 | Myers et al. |
| 5,630,829 | A | 5/1997 | Lauterjung |
| 5,632,771 | A | 5/1997 | Boatman et al. |
| 5,643,580 | A | 7/1997 | Subramaniam |
| 5,649,952 | A | 7/1997 | Lam |
| 5,697,971 | A | 12/1997 | Fischell et al. |
| 5,707,386 | A | 1/1998 | Schnepp-Pesch et al. |
| 5,716,365 | A | 2/1998 | Goicoechea et al. |
| 5,716,393 | A | 2/1998 | Lindenberg et al. |
| 5,718,713 | A | 2/1998 | Frantzen |
| 5,725,547 | A | 3/1998 | Chuter |
| 5,725,572 | A | 3/1998 | Lam et al. |
| 5,735,893 | A | 4/1998 | Lau et al. |
| 5,741,317 | A | 4/1998 | Ostrow |
| 5,741,327 | A | 4/1998 | Frantzen |
| 5,755,770 | A | 5/1998 | Ravenscroft |
| 5,755,776 | A | 5/1998 | Al-Saadon |
| 5,755,781 | A | 5/1998 | Jayaraman |
| 5,766,238 | A | 6/1998 | Lau et al. |
| 5,776,161 | A | 7/1998 | Globerman |
| 5,776,183 | A | 7/1998 | Kanesaka et al. |
| 5,800,520 | A | 9/1998 | Fogarty et al. |
| 5,800,521 | A | 9/1998 | Orth |
| 5,807,404 | A | 9/1998 | Richter |
| 5,810,872 | A | 9/1998 | Kanesaka et al. |
| 5,814,063 | A | 9/1998 | Freitag |
| 5,824,046 | A | 10/1998 | Smith et al. |
| 5,824,059 | A | 10/1998 | Wijay |
| 5,827,321 | A | 10/1998 | Roubin et al. |
| 5,836,966 | A | 11/1998 | St. Germain |
| 5,843,168 | A | 12/1998 | Dang |
| 5,855,597 | A | 1/1999 | Jayaraman |
| 5,855,600 | A | 1/1999 | Alt |
| 5,858,556 | A | 1/1999 | Eckert et al. |
| 5,861,027 | A | 1/1999 | Trapp |
| 5,868,780 | A | 2/1999 | Lashinski et al. |
| 5,873,906 | A | 2/1999 | Lau et al. |
| 5,876,432 | A | 3/1999 | Lau et al. |
| 5,879,381 | A | 3/1999 | Moriuchi et al. |
| 5,895,407 | A | 4/1999 | Jayaraman |
| 5,911,754 | A | 6/1999 | Kanesaka et al. |
| 5,913,895 | A | 6/1999 | Burpee et al. |
| 5,922,020 | A | 7/1999 | Klein et al. |
| 5,922,021 | A | 7/1999 | Jang |
| 5,925,061 | A | 7/1999 | Ogi et al. |
| 5,935,162 | A | 8/1999 | Dang |
| 5,938,697 | A | 8/1999 | Killion et al. |
| 5,948,016 | A | 9/1999 | Jang |
| 5,954,743 | A | 9/1999 | Jang |
| 5,980,553 | A | 11/1999 | Gray et al. |
| 5,984,929 | A | 11/1999 | Bashiri et al. |
| 6,001,123 | A | 12/1999 | Lau |

(56) References Cited

U.S. PATENT DOCUMENTS

| | | | |
|---|---|---|---|
| 6,013,854 A | 1/2000 | Moriuchi | |
| 6,017,365 A | 1/2000 | Von Oepen | |
| 6,022,371 A | 2/2000 | Killion | |
| 6,022,374 A | 2/2000 | Imran | |
| 6,027,527 A | 2/2000 | Asano et al. | |
| 6,042,597 A | 3/2000 | Kveen et al. | |
| 6,042,606 A | 3/2000 | Frantzen | |
| 6,053,941 A | 4/2000 | Lindenberg et al. | |
| 6,056,775 A | 5/2000 | Borghi et al. | |
| 6,059,822 A | 5/2000 | Kanesaka et al. | |
| 6,068,656 A | 5/2000 | Von Oepen | |
| 6,106,548 A | 8/2000 | Roubin et al. | |
| 6,113,627 A | 9/2000 | Jang | |
| 6,117,165 A | 9/2000 | Becker | |
| 6,129,755 A | 10/2000 | Mathis et al. | |
| 6,132,460 A | 10/2000 | Thompson | |
| 6,132,461 A | 10/2000 | Thompson | |
| 6,146,403 A | 11/2000 | St. Germain | |
| 6,162,245 A | 12/2000 | Jayaraman | |
| 6,168,619 B1 | 1/2001 | Dinh et al. | |
| 6,183,506 B1 | 2/2001 | Penn et al. | |
| 6,190,403 B1 | 2/2001 | Fischell et al. | |
| 6,190,406 B1 | 2/2001 | Duerig et al. | |
| 6,193,747 B1 | 2/2001 | Von Oepen | |
| 6,203,569 B1 | 3/2001 | Wijay | |
| 6,206,911 B1 | 3/2001 | Milo | |
| 6,210,429 B1 | 4/2001 | Vardi et al. | |
| 6,221,099 B1 | 4/2001 | Andersen et al. | |
| 6,231,598 B1 | 5/2001 | Berry et al. | |
| 6,245,101 B1 | 6/2001 | Drasler et al. | |
| 6,261,319 B1 | 7/2001 | Kveen et al. | |
| 6,264,685 B1 | 7/2001 | Ahari | |
| 6,264,688 B1 * | 7/2001 | Herklotz et al. | 623/1.16 |
| 6,272,370 B1 | 8/2001 | Gillies et al. | |
| 6,280,385 B1 | 8/2001 | Melzer et al. | |
| 6,287,331 B1 | 9/2001 | Heath | |
| 6,287,336 B1 | 9/2001 | Globerman et al. | |
| 6,290,721 B1 | 9/2001 | Heath | |
| 6,293,966 B1 | 9/2001 | Frantzen | |
| 6,299,635 B1 | 10/2001 | Frantzen | |
| 6,309,414 B1 | 10/2001 | Rolando et al. | |
| 6,312,459 B1 | 11/2001 | Huang et al. | |
| 6,315,791 B1 | 11/2001 | Gingras et al. | |
| 6,325,825 B1 | 12/2001 | Kula et al. | |
| 6,325,826 B1 | 12/2001 | Vardi et al. | |
| 6,327,772 B1 | 12/2001 | Zadno-Azizi et al. | |
| 6,330,884 B1 | 12/2001 | Kim | |
| 6,331,188 B1 | 12/2001 | Lau et al. | |
| 6,331,189 B1 | 12/2001 | Wolinsky et al. | |
| 6,331,190 B1 | 12/2001 | Shokoohi et al. | |
| 6,334,871 B1 | 1/2002 | Dor et al. | |
| 6,336,937 B1 | 1/2002 | Vonesh et al. | |
| 6,340,366 B2 | 1/2002 | Wijay | |
| 6,340,367 B1 | 1/2002 | Stinson et al. | |
| 6,348,065 B1 | 2/2002 | Brown et al. | |
| 6,355,057 B1 | 3/2002 | DeMarais et al. | |
| 6,355,058 B1 | 3/2002 | Pacetti et al. | |
| 6,358,274 B1 | 3/2002 | Thompson | |
| 6,361,557 B1 | 3/2002 | Gittings et al. | |
| 6,361,759 B1 | 3/2002 | Frayne et al. | |
| 6,379,381 B1 | 4/2002 | Hossainy et al. | |
| 6,395,020 B1 | 5/2002 | Ley et al. | |
| 6,402,777 B1 | 6/2002 | Globerman et al. | |
| 6,423,090 B1 | 7/2002 | Hancock | |
| 6,461,380 B1 | 10/2002 | Cox | |
| 6,471,720 B1 | 10/2002 | Ehr et al. | |
| 6,488,703 B1 | 12/2002 | Kveen et al. | |
| 6,520,987 B1 | 2/2003 | Plante | |
| 6,524,335 B1 | 2/2003 | Hartley et al. | |
| 6,524,336 B1 | 2/2003 | Papazolgou et al. | |
| 6,533,808 B1 | 3/2003 | Thompson | |
| 6,540,775 B1 | 4/2003 | Fischell et al. | |
| 6,540,777 B2 | 4/2003 | Stenzel | |
| 6,551,351 B2 | 4/2003 | Smith et al. | |
| 6,558,415 B2 | 5/2003 | Thompson | |
| 6,602,282 B1 | 8/2003 | Yan | |
| 6,610,086 B1 | 8/2003 | Kock et al. | |
| 6,613,081 B2 | 9/2003 | Kim et al. | |
| 6,629,994 B2 | 10/2003 | Gomez et al. | |
| 6,652,579 B1 | 11/2003 | Cox et al. | |
| 6,656,215 B1 | 12/2003 | Yanez et al. | |
| 6,663,664 B1 | 12/2003 | Pacetti | |
| 6,706,062 B2 | 3/2004 | Vardi et al. | |
| 6,730,117 B1 | 5/2004 | Tseng et al. | |
| 6,776,793 B2 | 8/2004 | Brown et al. | |
| 6,818,014 B2 | 11/2004 | Brown et al. | |
| 6,821,292 B2 | 11/2004 | Pazienza et al. | |
| 6,846,323 B2 | 1/2005 | Yip et al. | |
| 6,854,172 B2 | 2/2005 | Kaese et al. | |
| 6,878,162 B2 | 4/2005 | Bales et al. | |
| 6,962,603 B1 | 11/2005 | Brown et al. | |
| 6,969,402 B2 | 11/2005 | Bales et al. | |
| 6,981,986 B1 | 1/2006 | Brown et al. | |
| 7,014,654 B2 | 3/2006 | Welsh et al. | |
| 7,031,687 B2 | 4/2006 | Kivekas et al. | |
| 7,204,848 B2 | 4/2007 | Brown et al. | |
| 7,223,283 B2 | 5/2007 | Chouinard | |
| 7,243,408 B2 | 7/2007 | Vietmeier | |
| 7,329,277 B2 | 2/2008 | Addonizio et al. | |
| 7,331,986 B2 | 2/2008 | Brown et al. | |
| 7,354,450 B2 | 4/2008 | Bicek et al. | |
| 7,534,257 B2 | 5/2009 | Richter | |
| 7,842,080 B2 | 11/2010 | Chouinard | |
| 7,988,717 B2 | 8/2011 | Brown et al. | |
| 2001/0029397 A1 | 10/2001 | Thompson | |
| 2001/0039447 A1 | 11/2001 | Pinchasik et al. | |
| 2001/0044652 A1 | 11/2001 | Moore | |
| 2001/0056298 A1 | 12/2001 | Brown et al. | |
| 2002/0007212 A1 | 1/2002 | Brown et al. | |
| 2002/0022876 A1 | 2/2002 | Richter et al. | |
| 2002/0055770 A1 | 5/2002 | Doran et al. | |
| 2002/0095208 A1 | 7/2002 | Gregorich et al. | |
| 2002/0107562 A1 | 8/2002 | Hart et al. | |
| 2002/0111669 A1 | 8/2002 | Pazienza et al. | |
| 2002/0116049 A1 | 8/2002 | Girton et al. | |
| 2002/0120322 A1 | 8/2002 | Thompson et al. | |
| 2002/0123797 A1 | 9/2002 | Majercak | |
| 2002/0177893 A1 | 11/2002 | Brown et al. | |
| 2003/0004567 A1 | 1/2003 | Boyle et al. | |
| 2003/0018380 A1 | 1/2003 | Craig et al. | |
| 2003/0055485 A1 | 3/2003 | Lee et al. | |
| 2003/0176914 A1 | 9/2003 | Rabkin et al. | |
| 2003/0195606 A1 | 10/2003 | Davidson et al. | |
| 2003/0225448 A1 | 12/2003 | Gerberding | |
| 2004/0002753 A1 | 1/2004 | Burgermeister et al. | |
| 2004/0034402 A1 | 2/2004 | Bales et al. | |
| 2004/0044401 A1 | 3/2004 | Bales et al. | |
| 2004/0073291 A1 | 4/2004 | Brown et al. | |
| 2004/0088039 A1 | 5/2004 | Lee et al. | |
| 2004/0088044 A1 * | 5/2004 | Brown et al. | 623/1.16 |
| 2004/0111147 A1 | 6/2004 | Rabkin et al. | |
| 2004/0117002 A1 | 6/2004 | Girton et al. | |
| 2004/0143318 A1 | 7/2004 | Tseng | |
| 2004/0204751 A1 | 10/2004 | Fischell et al. | |
| 2005/0060025 A1 | 3/2005 | Mackiewicz et al. | |
| 2005/0107865 A1 * | 5/2005 | Clifford et al. | 623/1.16 |
| 2005/0149168 A1 * | 7/2005 | Gregorich | 623/1.15 |
| 2006/0015173 A1 * | 1/2006 | Clifford et al. | 623/1.16 |
| 2006/0052864 A1 | 3/2006 | Harder et al. | |
| 2006/0271159 A1 | 11/2006 | Gregorich et al. | |
| 2007/0150048 A1 | 6/2007 | Tischler | |
| 2007/0219624 A1 | 9/2007 | Brown et al. | |
| 2008/0097579 A1 | 4/2008 | Shanley et al. | |
| 2008/0221661 A1 | 9/2008 | Bidne et al. | |
| 2009/0163994 A1 | 6/2009 | Quigley et al. | |
| 2010/0100166 A1 | 4/2010 | Richter et al. | |
| 2012/0172972 A1 | 7/2012 | Meyer et al. | |
| 2012/0226342 A1 | 9/2012 | Mickley | |

FOREIGN PATENT DOCUMENTS

| | | |
|---|---|---|
| DE | 29702671 | 4/1997 |
| DE | 29708689 | 7/1997 |
| DE | 29708879 | 7/1997 |

(56) References Cited

FOREIGN PATENT DOCUMENTS

| | | |
|---|---|---|
| DE | 29716476 | 12/1997 |
| DE | 29816878 | 12/1998 |
| EP | 0364737 | 4/1990 |
| EP | 0364787 | 4/1990 |
| EP | 0540290 | 5/1993 |
| EP | 0541443 | 5/1993 |
| EP | 0606165 | 7/1994 |
| EP | 0679372 | 11/1995 |
| EP | 0796597 | 9/1997 |
| EP | 0800801 | 10/1997 |
| EP | 0801933 | 10/1997 |
| EP | 0821920 | 2/1998 |
| EP | 0876806 | 11/1998 |
| EP | 0897698 | 2/1999 |
| EP | 0970664 | 1/2000 |
| EP | 0983753 | 3/2000 |
| EP | 1034751 | 9/2000 |
| EP | 1159934 | 12/2001 |
| EP | 1190685 | 3/2002 |
| EP | 1362564 | 11/2003 |
| JP | 6004175 | 3/1994 |
| JP | 6181993 | 7/1994 |
| WO | 94/17754 | 8/1994 |
| WO | 96/21404 | 7/1996 |
| WO | 96/26689 | 9/1996 |
| WO | 96/28116 | 9/1996 |
| WO | 97/04721 | 2/1997 |
| WO | 97/14375 | 4/1997 |
| WO | 97/25937 | 7/1997 |
| WO | 97/32543 | 9/1997 |
| WO | 97/32544 | 9/1997 |
| WO | 97/33534 | 9/1997 |
| WO | 97/40780 | 11/1997 |
| WO | 97/40781 | 11/1997 |
| WO | 97/40782 | 11/1997 |
| WO | 97/40783 | 11/1997 |
| WO | 97/40784 | 11/1997 |
| WO | 97/40874 | 11/1997 |
| WO | 97/45073 | 12/1997 |
| WO | 98/20810 | 5/1998 |
| WO | 9826732 | 6/1998 |
| WO | 98/37833 | 9/1998 |
| WO | 98/47447 | 10/1998 |
| WO | 99/25273 | 5/1999 |
| WO | 99/44535 | 9/1999 |
| WO | 00/30563 | 6/2000 |
| WO | 01/32099 | 5/2001 |
| WO | 01/58386 | 8/2001 |
| WO | 02/060344 | 8/2002 |
| WO | 2004/032802 | 4/2004 |
| WO | 2008/005535 | 1/2008 |

OTHER PUBLICATIONS

Beyar, et al., "The BeStent; The Parallel-Serial Jang Stents", Handbook of Coronary Stents, Second Edition, 158-171 & 229-234 (1998).

Beyar, et al., "Newer Stents: Materials and Designs", IAGS Proceedings, 9(5): 363-371 (Jun. 1997).

Brochure Entitled "AVE Micro Stent TM", Instructions for Use, by Applied Vascular Engineering, Inc., pp. 1-15.

Brochure Entitled "Micro Stent TM", by Applied Vascular Engineering, Inc.

Brochure from Cook Incorporated regarding Gianturco-Rosch Biliary Z-Stents TM.

"Cambridge Dictionary of Science and Technology", Cambridge University Press, 128.

Carrasco et al., "Expandable Biliary Endoprosthesis: An Experimental Study", AJR, vol. 145, Dec. 1985, pp. 1279-1282.

Coons, Harold G. MD, "Self-expanding Stainless Steel Biliary Stents", Radiology 1989, vol. 170, No. 3, Part 2, pp. 979-983.

Irving et al., "Gianturco Expandable Metallic Biliary Stents: Results of a European Clinical Trial", Interventional Radiology, vol. 172, No. 2, Aug. 1989, pp. 321-326.

Japanese Infringement Search on Articulated Expandable Stents, Dated Jul. 12, 1995.

Kalpakjian, Serope "Manufacturing Processes for Engineering Materials", Illinois Institute of Technology, Adison-Wesley Publishing Company, pp. 340.

Levy, Stanley B. Ph.D. "Improved Dilatation Catheter Balloons", Journal of Clinical Engineering, vol. 11, No. 4, Jul.-Aug. 1986, pp. 291-296.

Melzer et al., "Performance Improvement of Surgical Instrumentation through the Use of Nitinol Materials", Proceedings of SMST-94 the First International Conference on Shape Memory and Superelastic Technologies, pp. 401-409 (Mar. 7-10, 1994).

Roberson et al., Engineering Fluid Mechanics, Third Edition, pp. 94 and pp. 414-421.

Roguin et al., "Acute and 30-Day Results of the Serpentine Balloon Expandable Stent Implantation in Simple and Complex Coronary Arterial Narrowings", The American Journal of Cardiology, 80:1155-1162 (Nov. 1997).

Roguin et al., "BeStent—The Serpentine Balloon Expandable Stent: Review of Mechanical Properties and Clinical Experiences", Artif Organs, 22(3):243-249 (Mar. 1998).

Schatz, Richard A. MD, "A View of Vascular Stents", Arizona Heart Institute Foundation, Phoenix, Arizona, Circulation, vol. 79, No. 2, Feb. 1989, pp. 445-457.

Sigwart, Ulrich "The Self-Expanding Mesh Stent", Section IV, Chapter 29, pp. 605-610.

"SMART TM Stent" Brochure, Cordis, a Johnson & Johnson company, date unknown.

Starck, E., "First Clinical Experience with the Memotherm Vascular Stent", Stents State of the Art Future Developments, pp. 59-62 (Jun. 1995).

Uchida et al., Technical Note Entitled "Modifications of Gianturco Expandable Wire Stents", AJR, vol. 150, May 1988, pp. 1185-1187.

Wallace et al., "Tracheobronchial Tree: Expandable Metallic Stents Used in Experimental and Clinical Applications, Work in Progress", Radiology, Feb. 1986, pp. 309-312.

U.S. Appl. No. 08/396,569, Brown, filed Mar. 1, 1995.
U.S. Appl. No. 60/076,946, filed Mar. 5, 1998, Tseng et al.
U.S. Appl. No. 10/474,848, Tseng et al., filed Dec. 29, 2003.
U.S. Appl. No. 61/448,843, filed Mar. 3, 2011, Bolsmier et al.

* cited by examiner

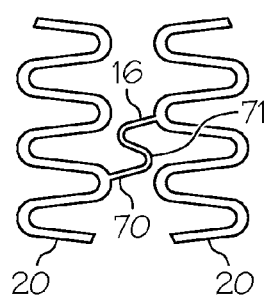 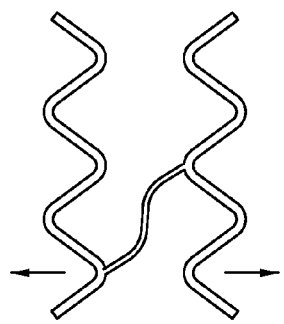
FIG. 3     FIG. 4
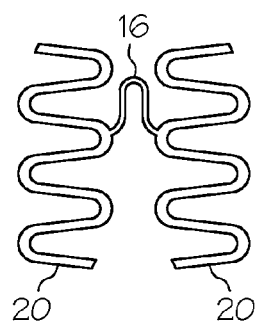 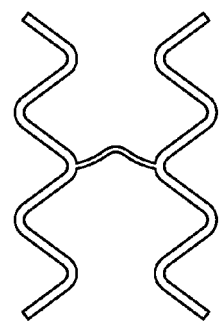
FIG. 5     FIG. 6
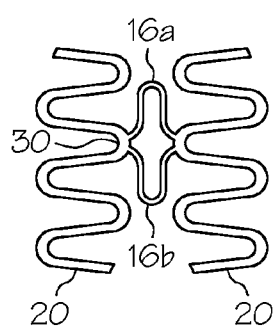 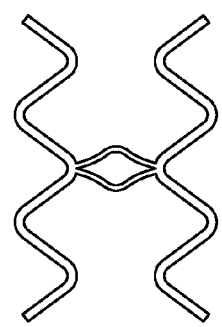
FIG. 7     FIG. 8
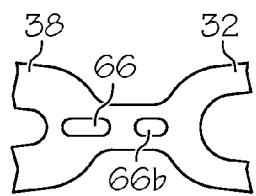 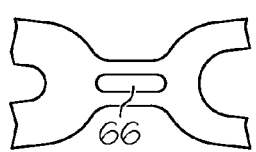 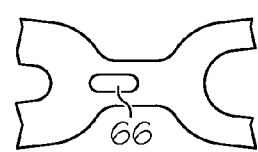
FIG. 10     FIG. 11     FIG. 12

LOW STRAIN HIGH STRENGTH STENT

CROSS-REFERENCE TO RELATED APPLICATIONS

This application claims priority to U.S. Patent Provisional Application No. 61/448,843 filed Mar. 3, 2011, the entire contents of which are hereby incorporated herein by reference.

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs that provide benefits over prior designs.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises an expandable framework comprising a plurality of serpentine bands and a plurality of connector struts. Each serpentine band comprises a plurality of alternating struts and turns. A plurality of the serpentine bands each have their proximal turns aligned on a common stent circumference and comprise first distal turns and second distal turns. The first distal turns are aligned with one another on a common stent circumference. The second distal turns aligned with one another on another common stent circumference. Each band in the plurality comprises first struts and second struts. Each first strut is attached between a proximal turn and a first distal turn, and each second strut is attached between a proximal turn and a second distal turn. The second struts are wider than said first struts. Each connector strut is attached between a second distal turn of one serpentine band and a proximal turn of an adjacent serpentine band.

In at least one embodiment, a stent comprises an expandable framework comprising a plurality of serpentine bands and a plurality of connector struts. Each serpentine band comprises a plurality of alternating struts and turns. A plurality of the serpentine bands each have their proximal turns aligned on a common stent circumference and comprise first distal turns and second distal turns. The first distal turns are aligned with one another on a common stent circumference. The second distal turns aligned with one another on another common stent circumference. A distal end band comprises first proximal turns, second proximal turns and distal turns. The distal turns are aligned with one another on a common stent circumference. The first proximal turns are aligned with one another on a common stent circumference, and the second proximal turns are aligned with one another on another common stent circumference. Each connector strut is attached between a second distal turn of one serpentine band and a proximal turn of an adjacent serpentine band.

In at least one embodiment, a stent comprises an expandable framework comprising at least one serpentine band pair comprising a first serpentine band and a second serpentine band. Each serpentine band comprises a plurality of alternating struts and turns. Adjacent serpentine bands are connected by at least one connector strut. The first serpentine band includes proximal turns aligned on a common stent circumference and comprises first distal turns and second distal turns. The first distal turns are aligned with one another on a common stent circumference. The second distal turns aligned with one another on another common stent circumference. The second serpentine band comprises first proximal turns, second proximal turns and distal turns. The distal turns are aligned with one another on a common stent circumference. The first proximal turns are aligned with one another on a common stent circumference, and the second proximal turns are aligned with one another on another common stent circumference. In some embodiments, a stent comprises a plurality of said serpentine band pairs.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 3 shows an embodiment of a connector strut.

FIG. 4 shows the connector strut of FIG. 3 in another configuration.

FIG. 5 shows another embodiment of a connector strut.

FIG. 6 shows the connector strut of FIG. 5 in another configuration.

FIG. 7 shows an embodiment of a connector strut pair.

FIG. 8 shows the connector strut pair of FIG. 7 in another configuration.

FIGS. 10-12 show embodiments of strain relief cell configurations.

DETAILED DESCRIPTION OF THE INVENTION

Figure 1:
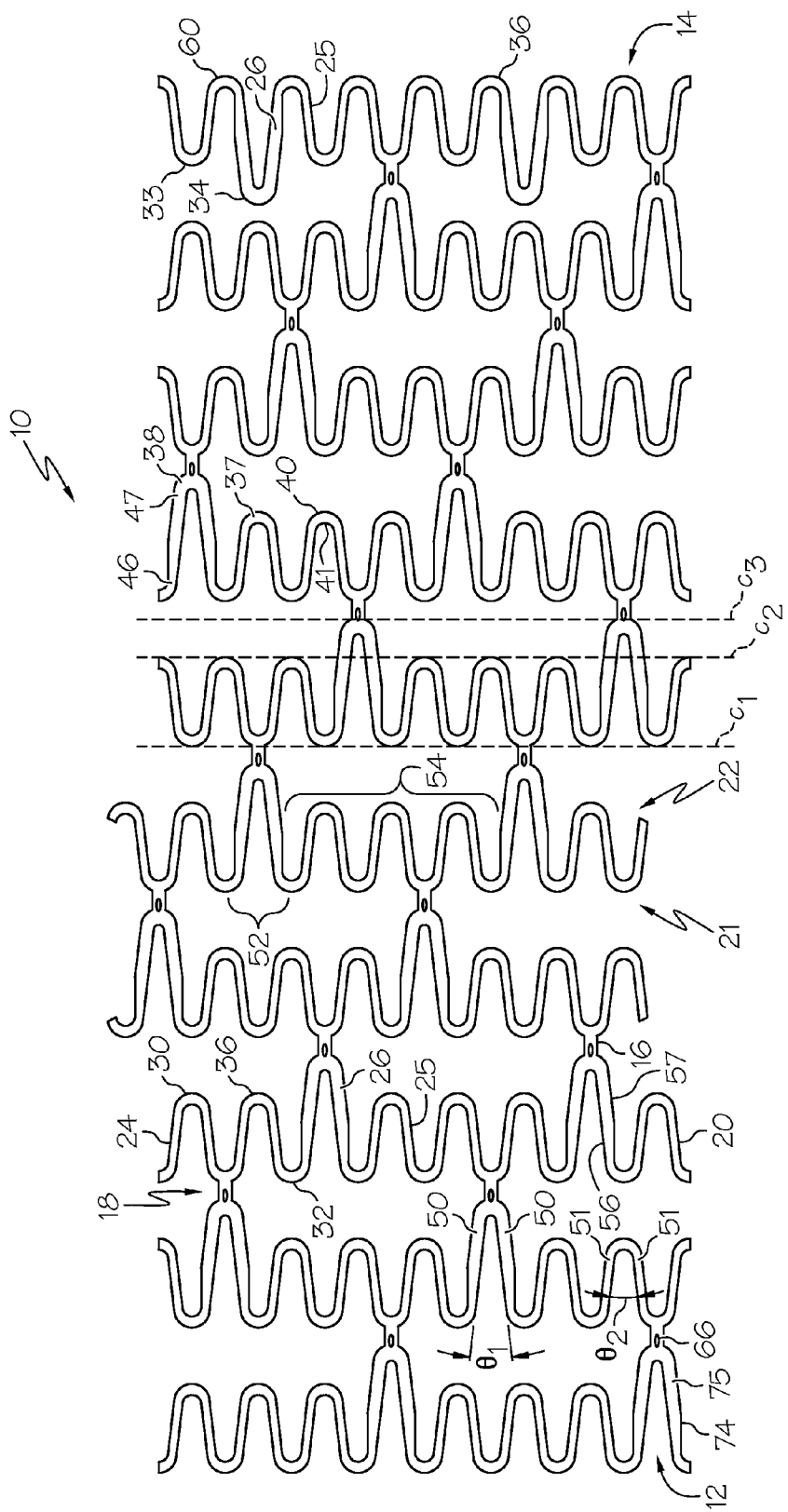
FIG. 1 shows a flat pattern for an embodiment of a stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows a flat pattern for an embodiment of a stent 10. The stent 10 comprises an expandable framework having a tubular shape. The framework is expandable from an expanded configuration to an expanded configuration having a larger size (e.g. larger diameter). The stent 10 includes a proximal end 12 and a distal end 14.

The framework comprises serpentine bands 20 and connector struts 16. The connector struts 16 connect between adjacent serpentine bands 20. In some embodiments, a plurality of connectors 16 comprise a connector column 18, and the stent 10 includes serpentine bands 20 and connector columns 18 that alternate along the length of the stent 10. In some embodiments, a connector column 18 excludes other portions of the stent framework, such as serpentine bands 20.

Desirably, each serpentine band 20 comprises a closed structure having a tubular shape. Each serpentine band 20 defines a proximal end 21 and a distal end 22. Each serpentine band 20 comprises alternating struts 24 and turns 30. Each strut 24 spans between two turns 30. Desirably, the turns 30 comprise alternating proximal turns 32 and distal turns 36, wherein the proximal turns 32 are located at the proximal end 21 of the band 20 and the distal turns 36 are located at the distal end 22 of the band 20.

A turn 30 is generally at least as wide as a strut 24 to which the turn 30 connects. As shown in FIG. 1, the turns 30 are typically wider than the struts 24 to which the turn 30 connects. Desirably, the width of a turn 30 amounts to 1.0-1.3 times the width of the struts 24 to which the turn 30 connects.

In some embodiments, all of the proximal turns 32 of a serpentine band 20 are aligned with one another on a common circumference $c_1$.

In some embodiments, the distal turns 36 of a serpentine band 20 comprise first distal turns 37 and second distal turns 38. Within the band 20, the first distal turns 37 are aligned with one another on a common circumference $c_2$. The second distal turns 38 are similarly aligned with one another on a common circumference $c_3$ that is offset from the common circumference $c_2$ of the first distal turns 37.

In some embodiments, each connector strut 16 is attached between a second distal turn 38 of one serpentine band 20 and a proximal turn 32 of an adjacent serpentine band 20. In some embodiments, the connector struts 16 do not attach to any first distal turns 37.

In some embodiments, the second distal turns 38 are wider than the first distal turns 37. As shown in FIG. 1, the second distal turns 38 are approximately 50% wider than (approximately 1.5 times the width of) the first distal turns 37. Desirably, the second distal turns 38 have a width ranging from 40%-60% wider than (approximately 1.4-1.6 times the width of) the first distal turns 37.

In some embodiments, an outside portion 40 of the second distal turns 38 has the same radius of curvature as an outside portion 40 of the first distal turns 37. In some embodiments, an inside portion 41 of the second distal turns 38 has a smaller radius of curvature than an inside portion 41 of the first distal turns 37.

In some embodiments, the first distal turns 37 comprise the same width as the proximal turns 32. In some embodiments, the outside portions 40 of first distal turns 37 and proximal turns 32 have a similar radius of curvature, and the inside portions 41 of first distal turns 37 and proximal turns 32 have a similar radius of curvature.

In some embodiments, the serpentine bands 20 comprise first struts 25 and second struts 26. Each first strut 25 extends between a proximal turn 32 and a first distal turn 37. Each second strut 26 extends between a proximal turn 32 and a second distal turn 38.

In some embodiments, the second struts 26 are longer than the first struts 25. As shown in FIG. 1, the second struts 26 are approximately 50% longer than (approximately 1.5 times the length of) the first struts 25. Desirably, the second struts 26 have a length ranging from 50%-70% longer than (approximately 1.5-1.7 times the length of) the first struts 25.

In some embodiments, the second struts 26 are wider than the first struts 25. In some embodiments, the second struts 26 are tapered and comprise a greater width at one end. For example, in some embodiments, a second strut 26 is attached at a first end 46 to a proximal turn 32 and is attached at a second end 47 to a second distal turn 38. The second end 47 comprises a greater width than the first end 46, and the strut 26 is tapered along its length. Thus, the first end 46 is narrower than the second end 47. In some embodiments, the first end 46 comprises the same width as the width of the first struts 25.

In some embodiments, the first distal turns 37 have the same width as the first struts 25. In some embodiments, the second distal turns 38 have the same width as the second struts 26.

In some embodiments, a second strut 26 comprises a tapered portion 74 and a non-tapered portion 75. The sidewalls of the non-tapered portion 75 extend parallel to one another, whereas the sidewalls of the tapered portion 74 are non-parallel. In some embodiments, the tapered portion 74 comprises one-half of the length of the second strut 26, and the non-tapered portion 75 comprises one-half of the length.

In some embodiments, a first side 56 of a second strut 26 is straight along its length, and a second side 57 of the second strut 26 is not straight. For example, the second side 57 can comprise two straight portions that are non-parallel.

In some embodiments, a serpentine band 20 defines one or more stronger strut pairs 50. A stronger strut pair 50 comprises a pair of second struts 26 and a second distal turn 38 that collectively provide a greater resistance to stent expansion than other portions of the serpentine band 20, such as the first struts 25 and the first distal turns 37. When a serpentine band 20 includes one or more stronger strut pairs 50, the remainder of the serpentine band 20 will experience expansion/deformation prior to the expansion/deformation of the stronger strut pair(s) 50. This encourages the remainder of the serpentine band 20 to achieve a predetermined expanded shape, desirably prior to deformation of the stronger strut pair(s) 50.

Desirably, the stronger strut pair(s) 50 of adjacent serpentine bands 20 are not aligned with one another in a stent longitudinal direction. Thus, stronger strut pair(s) 50 of adjacent serpentine bands 20 are offset from one another in a stent circumferential direction.

In some embodiments, a serpentine band 20 comprises at least one stronger portion 52 and at least one weaker portion 54. Generally, a stronger portion 52 provides a greater resistance to stent expansion than a weaker portion 54. In some embodiments, a stronger portion 52 comprises a second distal turn 38 that is wider than turns 30 in the weaker portion(s) 54. In some embodiments, a stronger portion 52 comprises a second distal turn 38 and at least one second strut 26, which comprise portions that are wider than turns 30 and struts 24 in the weaker portion(s) 54. In some embodiments, a weaker portion 54 comprises at least one turn 30 and a plurality of struts 24. In some embodiments, a weaker portion 54 comprises proximal turns 32, first struts 25 and first distal turns 37.

In some embodiments, a weaker portion 54 comprises one or more weaker strut pairs 51. While a stronger strut pair 50 can connect to a second distal turn 38, a weaker strut pair 51 generally connects to a first distal turn 37. In some embodiments, a weaker strut pair 51 also comprises the first distal turn 37 connected to the pair of struts.

In some embodiments, a plurality of weaker strut pairs 51 are provided for each stronger strut pair 50. As shown in FIG. 1, a serpentine band 20 comprises three weaker strut pairs 51 for each stronger strut pair 50 (e.g. a ratio of 3:1). In other embodiments, a serpentine band 20 can include more or less weaker strut pairs 51 for each stronger strut pair 50 (ratios of 2:1, 4:1, 6:1, 8:1, etc. are contemplated, as well as any other suitable ratio).

In some embodiments, the stent 10 comprises a plurality of serpentine bands 20 having a similar shape/configuration. FIG. 1 shows several serpentine bands 20 that have the same shape/configuration, but have different rotational orientations along the length of the stent 10.

In some embodiments, the stent 10 comprises a plurality of similarly shaped bands combined with a unique distal end band 60. In some embodiments, a distal end band 60 can be considered reversed with respect to the other serpentine bands 20, for example comprising similar features in a mirror-image configuration. In some embodiments, all of the distal turns 36 of the distal end band 60 are aligned on a common stent circumference. In some embodiments, a distal end band 60 comprises first proximal turns 33 and second proximal turns 34. The first proximal turns 33 are aligned with one another on a common circumference, and the second proximal turns 34 are aligned with one another on a common circumference that is offset from the common circumference of the first proximal turns 33.

In some embodiments, a distal end band 60 comprises first struts 25 and second struts 26. In some embodiments, a pair of second struts 26 and a second proximal turn 34 comprise a stronger strut pair 50.

Desirably, the distal end band 60 is attached to the stent 10 by one or more connector struts 16 that each attach to first proximal turn 33. Desirably, the second proximal turns 34 of the distal end band 60 are not connected to a connector strut 16.

Figure 2:
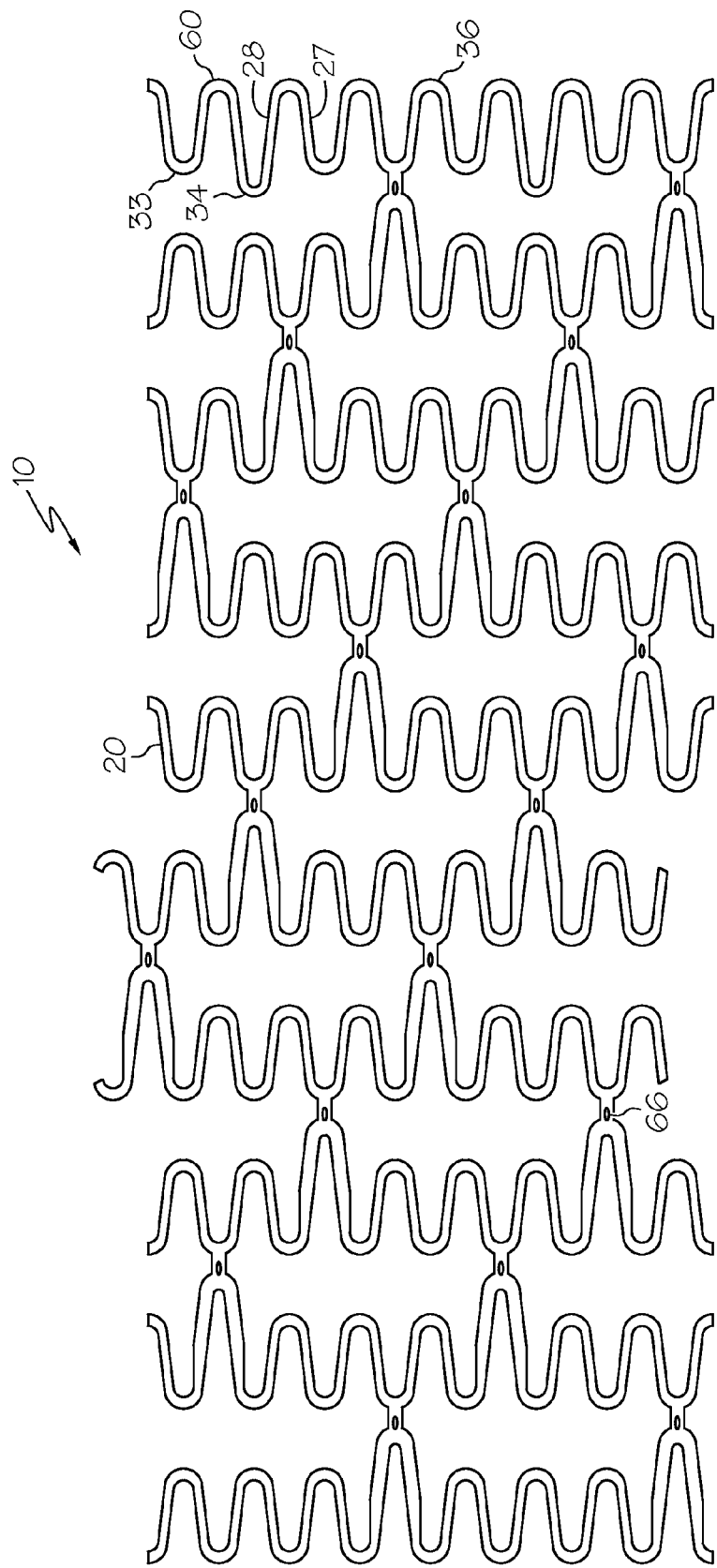
FIG. 2 shows a flat pattern for another embodiment of a stent.

FIG. 2 shows another embodiment of a stent 10. The stent 10 of FIG. 2 includes serpentine bands 20 that are generally similar to the serpentine bands 20 shown in FIG. 1. FIG. 2 includes a distal end band 60 that is different from FIG. 1.

The distal end band 60 of FIG. 2 includes distal turns 36 that are aligned on a common circumference, as well as first proximal turns 33 and second proximal turns 34. The first proximal turns 33 are aligned with one another on a common circumference, and the second proximal turns 34 are aligned with one another on a common circumference that is offset from the common circumference of the first proximal turns 33. In some embodiments, the second proximal turns 34 comprise the same width as the first proximal turns 33, which may have the same width as the distal turns 36. In some embodiments, the distal end band 60 comprises longer struts 28 and shorter struts 27. In some embodiments, the longer struts 28 and the shorter struts 27 comprise the same width.

FIGS. 3 and 4 show another embodiment of a connector strut 16 at different stages of expansion. In some embodiments, a connector strut 16 comprises an "S" shape. In some embodiments, a connector strut includes a plurality of straight portions 70 and a plurality of curved portions 71 in at least the unexpanded state. In some embodiments, a connector strut 16 comprises multiple portions that are oriented on a common stent circumference. For example, as shown in FIG. 3, the connector strut 16 includes a plurality of straight portions 70 that would each be intersected by a common stent circumference. Such a connector strut 16 can reorient during stent expansion such that no two portions of the connector strut 16 are oriented on a common circumference, for example as shown in FIG. 4.

In some embodiments, a serpentine band 20 can experience foreshortening during expansion (e.g. the proximal end 21 and distal end 22—see FIG. 1—of the serpentine band 20 move closer to one another during expansion, and the serpentine band 20 in the expanded state occupies a shorter length portion of the stent 10 than in the unexpanded state). In some embodiments, the connector struts 16 are configured to expand in the stent lengthwise direction an amount approximately equal to the foreshortening of the serpentine bands 20.

FIGS. 5 and 6 show another embodiment of a connector strut 16 at different stages of expansion. In some embodiments, a connector strut 16 comprises a "U" shape.

FIGS. 7 and 8 show another configuration of connector struts 16 at different stages of expansion. FIGS. 7 and 8 include a connector strut 16 that is generally similar the connector strut of FIGS. 5 and 6, characterized as a first connector strut 16a. FIGS. 6 and 7 further include a second connector strut 16b that connects between the same turns 30 as the first connector strut 16a. In some embodiments, the second connector strut 16b comprises a mirror image of the first connector strut 16a. In some embodiments, the first connector strut 16a connects to upper portions of the turns 30, and the second connector strut 16b connects to lower portions of the turns 30.

Figure 9:
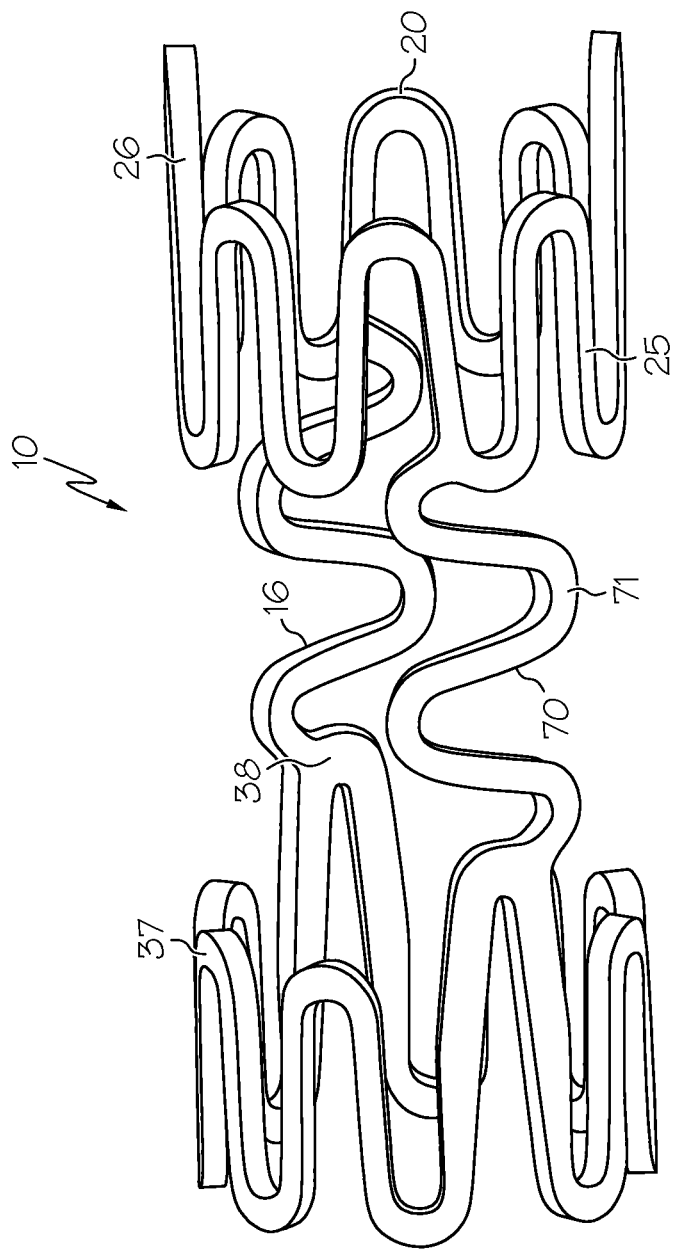
FIG. 9 shows another connector configuration and serpentine bands in tubular form.

FIG. 9 shows an embodiment of a stent 10 in tubular form. In some embodiments, the connectors 16 include a plurality of straight portions 70 and a plurality of curved portions 71. As shown in FIG. 9, each connector 16 comprises four curved portions 71 and three elongate straight portions 70.

FIGS. 10-12 show examples of strain relief cells 66 formed in portions of the stent 10. Further examples of strain relief cells 66 are shown in FIGS. 1 and 2. In some embodiments, a strain relief cell 66 is formed in a connector strut 16. In some embodiments, each connector strut 16 of the stent 10 includes a strain relief cell 66.

In some embodiments, a strain relief cell 66 extends into a portion of a second distal turn 38. In some embodiments, a connector strut 16 further includes a second strain relief cell 66b, for example as shown in FIG. 10. In some embodiments, a strain relief cell 66 extends an entire length of a connector strut 16, for example as shown in FIG. 11.

In some embodiments, the stent 10 consists of the elements depicted in FIG. 1 or FIG. 2. In some embodiments, a serpentine band 20 consists of the elements depicted within a serpentine band 20 depicted in FIG. 1 or FIG. 2.

The stent patterns disclosed herein are particularly suited to materials that are generally considered to have a relatively low yield strength and relatively low ductility when compared to traditional stent materials. For example, the stent patterns disclosed herein are well suited for stents formed from magnesium.

As used in this application, a stent having a relatively low yield strength comprises a material having a tensile yield strength of 30 ksi (30,000 psi) or less.

As used in this application, a stent having a relatively low ductility will comprise a material that experiences less than 30% elongation to fracture in tension.

Figure 13:
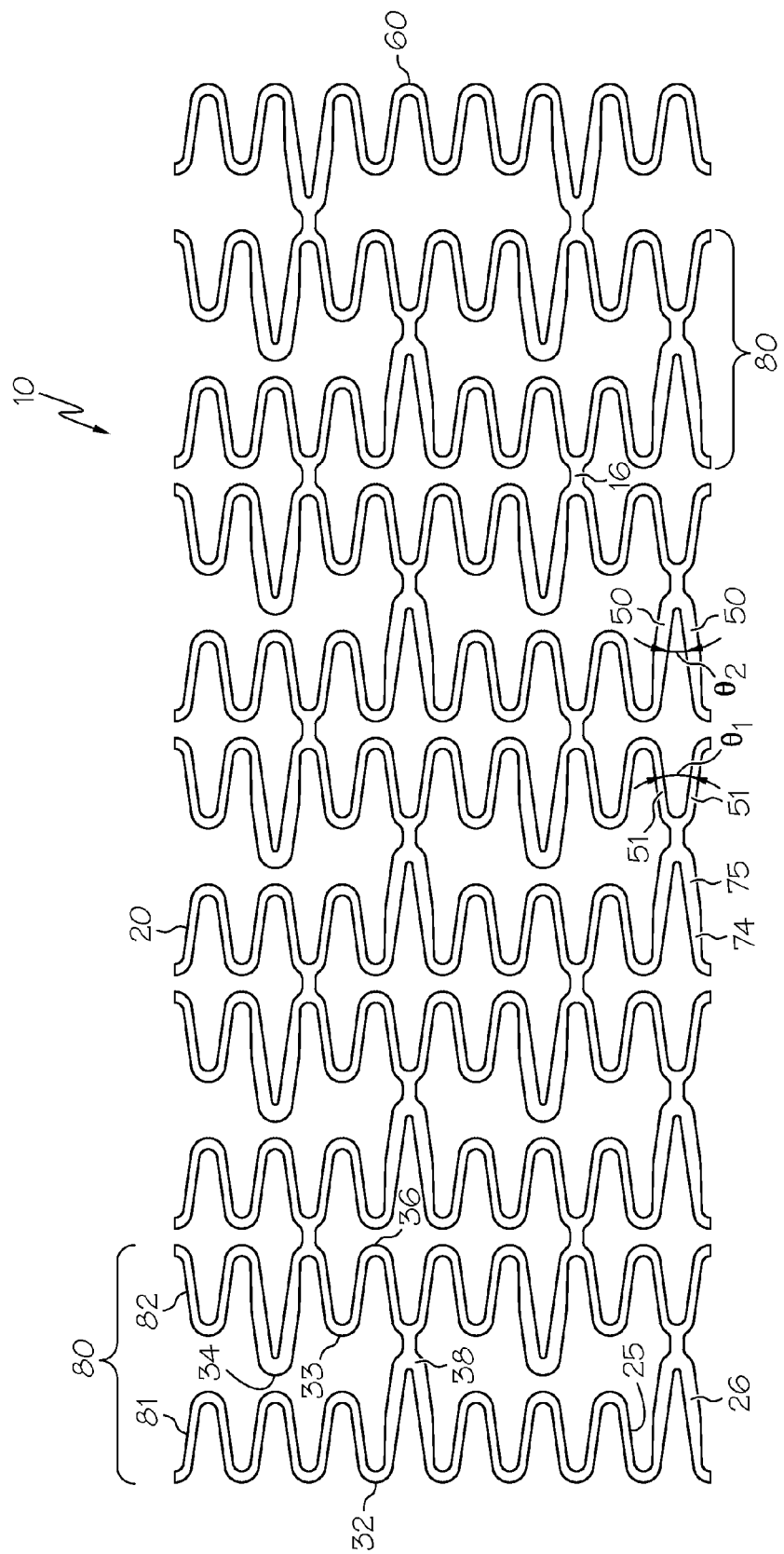
FIG. 13 shows a flat pattern for another embodiment of a stent.

FIG. 13 shows a flat pattern for another embodiment of a stent 10. In some embodiments, a stent 10 comprises at least one serpentine band pair 80. FIG. 13 includes a plurality of serpentine band pairs 80, as well as a distal end band 60 as previously described herein.

Desirably, a serpentine band pair 80 comprises a first serpentine band 81 and a second serpentine band 82. Desirably, a first serpentine band 81 is configured similarly to serpentine bands 20 as previously described herein (e.g. similar to most of the serpentine bands 20 shown in FIG. 1). Desirably, a second serpentine band 82 is configured similarly to the distal end band 60 as described with respect to FIG. 1.

Thus, a first serpentine band 81 desirably includes proximal turns 32 that are aligned on a common stent circumference (see e.g. $c_1$ in FIG. 1), a plurality of first distal turns 37 that are aligned on another common stent circumference (see e.g. $c_2$ in FIG. 1) and a plurality of second distal turns 38 that are aligned on another common stent circumference (see e.g. $c_3$ in FIG. 1). A first serpentine 81 comprises first struts 25 and second struts 26 as previously described herein.

A second serpentine band 82 desirably includes distal turns 36 that are aligned on a common stent circumference, a plurality of first proximal turns 33 that are aligned on another common stent circumference and a plurality of second proximal turns 34 that are aligned on another common stent circumference. A second serpentine 82 comprises first struts 25 and second struts 26 as previously described herein.

Desirably, the serpentine bands 81, 82 of a serpentine band pair 80 are aligned such that turns of the first serpentine band 81 are aligned with turns of the second serpentine band 82 in a stent longitudinal direction. Desirably, the bands 81, 82 are aligned such that the second struts 26 of the first band 81 are located midway between the second struts 26 of the second band 82. For example, a second distal turn 38 of the first band 81 is located midway between the second proximal turns 34 of the second band 82.

In some embodiments, the second distal turns 38 and second proximal turns 34 of a serpentine band pair 80 overlap longitudinally (e.g. a common stent circumference will intersect the second distal turns 38 and the second proximal turns 34).

Desirably, adjacent serpentine band pairs 80 are connected by at least one connector 16.

Figure 14:
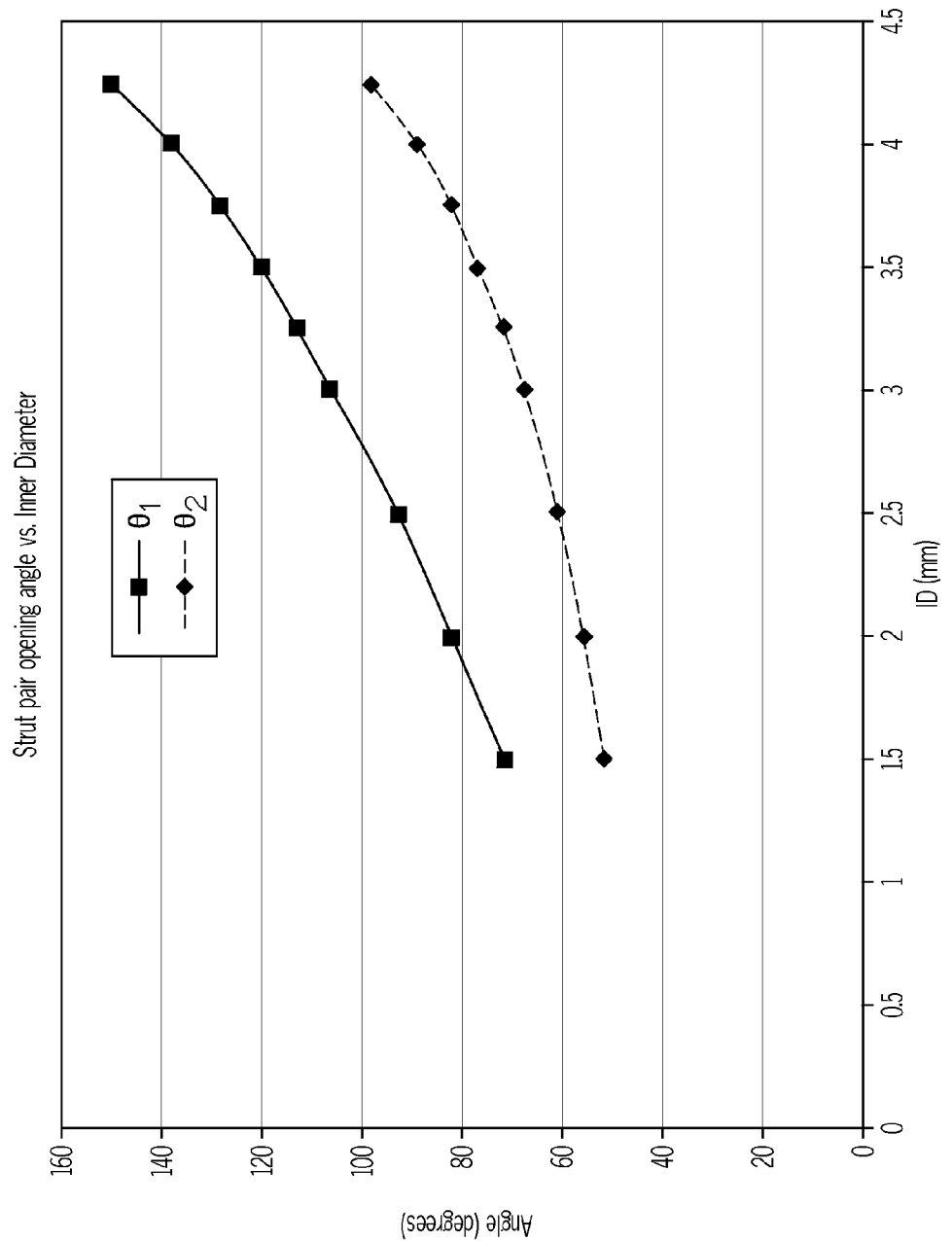
FIG. 14 shows a graph comparing an angle between the struts included in stronger and weaker strut pairs at various stages of expansion.

FIG. 14 shows a graph comparing strut pair angles at various stages of expansion. The stents 10 disclosed herein that include stronger strut pairs 50 and weaker strut pairs 51 will generally exhibit a greater amount of shape change during expansion from the weaker strut pairs 51, as the turns (e.g. first distal turns 37) that connect the weaker strut pairs 51 typically deform at lower stresses than the turns (e.g. second distal turns 38) that connect the stronger strut pairs 50. An angle $\theta_1$ between the struts 26 of a stronger strut pair 50 is the stronger strut pair angle $\theta_1$. An angle $\theta_2$ between the struts 25 of a weaker strut pair 51 is the weaker strut pair angle $\theta_2$. As shown in FIG. 14, the weaker strut pair angle $\theta_2$ is generally greater than the stronger strut pair angle $\theta_1$. In some embodiments, the strut pair angles $\theta_1$, $\theta_2$ are measured between a central axis of each strut of the strut pair. In some embodiments, the strut pair angles $\theta_1$, $\theta_2$ are measured between straight first sides 56 of each strut of the strut pair, for example when the struts are tapered, wherein the strut pair angles $\theta_1$, $\theta_2$ comprise the inner angles between the struts (e.g. 25, 26) of a strut pair (e.g. 50, 51).

The inventive stents may be made from any suitable biocompatible materials including one or more polymers, one or more metals or combinations of polymer(s) and metal(s). Examples of suitable materials include biodegradable materials that are also biocompatible. In some embodiments, a stent can have one or more components constructed from one or more metals, polymers or combinations thereof that are corrodible so as to dissolve, dissociate or otherwise break down in the body without ill effect. Examples of such materials have been referred to as being degradable, biodegradable, biologically degradable, erodable, bioabsorbable, bioresorbable, and the like. Biodegradable material will generally undergo breakdown or decomposition into harmless compounds as part of a normal biological process. Suitable biodegradable materials include polylactic acid, polyglycolic acid (PGA), collagen or other connective proteins or natural materials, polycaprolactone, hyaluric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, iron, Niobium, gold and alloys of any of the above-mentioned metals. Examples of suitable alloys include platinum-iridium alloys, stainless steel-platinum alloys, cobalt-chromium alloys including Elgiloy and Phynox, MP35N alloy and nickel-titanium alloys, for example, Nitinol. Additional biodegradable alloys, such as magnesium alloys and zinc alloys, Fe—Mn, Fe—Mn—Pd, Mg, Mg—Zn, Mg—Al, Mg—RE (rare earth elements, e.g. Nd, Y, etc.) are suitable, and some examples are discussed in U.S. Pat. No. 6,854,172 and US 2006/0052864, the entire contents of which are hereby incorporated herein by reference.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to."

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising:
an expandable framework comprising multiple serpentine bands and a plurality of connector struts, each connector strut attached between two adjacent serpentine bands;
each serpentine band comprising a plurality of alternating struts and turns, said turns comprising alternating proximal turns and distal turns, each serpentine band forming a closed tubular structure;
a plurality of said serpentine bands each having their proximal turns aligned on a common stent circumference and comprising first distal turns and second distal turns, the first distal turns aligned with one another on a common stent circumference, the second distal turns aligned with one another on a common stent circumference and offset from the first distal turns;
a distal end band comprising struts, first proximal turns, second proximal turns and distal turns, the distal turns aligned with one another on a common stent circumference, the first proximal turns aligned with one another on a common stent circumference, the second proximal turns aligned with one another on a common stent circumference and offset from the first proximal turns, at least one strut of the distal end band comprising a tapered portion and a non-tapered portion;
each connector strut attached between one of the second distal turns of one serpentine band and one of the proximal turns of an adjacent serpentine band.

2. The stent of claim 1, wherein there is at least one distal connector strut attached between one of the second distal turns of one serpentine band and one of the first proximal turns of said distal end band.

3. The stent of claim 1, wherein each band in said plurality of serpentine bands comprises first struts and second struts, each first strut attached between one of the proximal turns and one of the first distal turns, each second strut attached between one of the proximal turns and one of the second distal turns, said second struts being wider than said first struts.

4. The stent of claim 3, wherein each second strut tapers from a wider end attached to one of the second distal turns to a narrower end attached to one of the proximal turns.

5. The stent of claim 4, wherein at least one of the second struts comprises a tapered portion and a non-tapered portion.

6. A stent comprising:
an expandable framework comprising multiple serpentine bands and a plurality of connector struts, each connector strut attached between two adjacent serpentine bands;

each serpentine band comprising a plurality of alternating struts and turns, said turns comprising alternating proximal turns and distal turns, each serpentine band forming a closed tubular structure;

a plurality of said serpentine bands each having their proximal turns aligned on a common stent circumference and comprising first distal turns and second distal turns, the first distal turns aligned with one another on a common stent circumference, the second distal turns aligned with one another on a common stent circumference and offset from the first distal turns, each serpentine band in said plurality comprising first struts and second struts, each first strut attached between one of the proximal turns and one of the first distal turns, each second strut attached between one of the proximal turns and one of the second distal turns, said second struts being wider than said first struts;

each connector strut attached between one of the second distal turns of one serpentine band and one of the proximal turns of an adjacent serpentine band; and a distal end band having first proximal turns, second proximal turns and distal turns, the distal turns aligned with one another on a common stent circumference, the first proximal turns aligned with one another on a common stent circumference, the second proximal turns aligned with one another on a common stent circumference and offset from the first proximal turns.

7. The stent of claim 1, wherein there is at least one distal connector strut attached between one of the second distal turns of one serpentine band and one of the first proximal turns of said distal end band.

8. The stent of claim 1, wherein the distal end band comprises shorter struts and longer struts, the shorter struts and the longer struts having the same width.

9. The stent of claim 1, wherein said second distal turns have a greater width than said first distal turns.

10. The stent of claim 9, wherein the second distal turns are 40%-60% wider than the first distal turns.

11. The stent of claim 1, wherein a said second strut is 50%-70% longer than a said first strut.

12. The stent of claim 1, wherein each second strut tapers from a wider end attached to one of the second distal turns to a narrower end attached to one of the proximal turns.

13. The stent of claim 12, wherein the narrower end of each second strut comprises the same width as one of the first struts.

14. The stent of claim 1, wherein connector columns are located between adjacent serpentine bands, each connector column including the connector struts and excluding serpentine bands.

15. The stent of claim 1, wherein each connector strut comprises a strain relief cell.

16. The stent of claim 15, wherein a strain relief cell extends into a portion of a second distal turn.

17. The stent of claim 1, wherein each connector strut comprises a curved portion.

18. A stent comprising:

an expandable framework comprising multiple serpentine bands and a plurality of connector struts, each connector strut attached between two adjacent serpentine bands;

each serpentine band comprising a plurality of alternating struts and turns, said turns comprising alternating proximal turns and distal turns, each serpentine band forming a closed tubular structure;

a plurality of said serpentine bands each having their proximal turns aligned on a common stent circumference and comprising first distal turns and second distal turns, the first distal turns aligned with one another on a common stent circumference, the second distal turns aligned with one another on a common stent circumference and offset from the first distal turns, each serpentine band in said plurality comprising first struts and second struts, each first strut attached between one of the proximal turns and one of the first distal turns, each second strut attached between one of the proximal turns and one of the second distal turns said second struts being wider than said first struts, each second strut tapering from a wider end attached to one of the second distal turns to a narrower end attached to one of the proximal turns;

each connector strut attached between a second distal turn of one serpentine band and a proximal turn of an adjacent serpentine band;

wherein at least one of said second struts comprises a tapered portion and a non-tapered portion, and the non-tapered portion comprises half of the length of the second strut.

* * * * *